(12) United States Patent
McCormick et al.

(10) Patent No.: US 10,842,963 B2
(45) Date of Patent: Nov. 24, 2020

(54) INTUBATION STYLET WITH VIDEO FEED

(71) Applicant: Brio Device, LLC, Ann Arbor, MI (US)

(72) Inventors: Laura McCormick, Ann Arbor, MI (US); Gregg D. Niven, Kaysville, UT (US)

(73) Assignee: Brio Device, LLC, Ann Arbor, MI (US)

( * ) Notice: Subject to any disclaimer, the term of this patent is extended or adjusted under 35 U.S.C. 154(b) by 443 days.

(21) Appl. No.: 15/737,336

(22) PCT Filed: Jun. 29, 2017

(86) PCT No.: PCT/US2017/039966
§ 371 (c)(1),
(2) Date: Dec. 18, 2017

(87) PCT Pub. No.: WO2018/005776
PCT Pub. Date: Jan. 4, 2018

(65) Prior Publication Data
US 2018/0250484 A1 Sep. 6, 2018

Related U.S. Application Data

(60) Provisional application No. 62/357,602, filed on Jul. 1, 2016.

(51) Int. Cl.
*A61B 1/00* (2006.01)
*A61M 16/04* (2006.01)
(Continued)

(52) U.S. Cl.
CPC ....... *A61M 16/0488* (2013.01); *A61B 1/0052* (2013.01); *A61B 1/05* (2013.01); *A61B 1/267* (2013.01); *A61B 1/2733* (2013.01)

(58) Field of Classification Search
CPC .... A61B 1/00179; A61B 1/267; A61B 1/0052
See application file for complete search history.

(56) References Cited

U.S. PATENT DOCUMENTS 4,483,326 A * 11/1984 Yamaka ............... A61B 1/0057
600/141
5,318,008 A * 6/1994 Bullard ............... A61B 1/0056
600/139
(Continued)

FOREIGN PATENT DOCUMENTS

EP 2606812 A1 6/2013
WO 2016082450 A1 6/2016

*Primary Examiner* — Alexandra L Newton
*Assistant Examiner* — Rynae Boler
(74) *Attorney, Agent, or Firm* — Endurance Law Group PLC

(57) ABSTRACT

A manually articulated stylet assembly for placing an endotracheal tube. The stylet assembly has a steering shaft that carries a flexible distal tip at one end and is attached to a handle at the other end. The distal tip is manipulated via sheathed cables controlled by a remote actuator in the handle. A biasing member inside the remote actuator maintains continuous tension on the cables to improve control. A video camera is carried in a recessed lens pocket in the steering shaft but spaced from the distal tip. The camera FOV captures movement of the distal tip with foreshortened perspective. A collar seat in the handle receives the collar connector of a standard endotracheal tube, providing quick disconnect when removing the stylet assembly upon placement.

17 Claims, 9 Drawing Sheets

(51) Int. Cl.
  *A61B 1/273* (2006.01)
  *A61B 1/005* (2006.01)
  *A61B 1/05* (2006.01)
  *A61B 1/267* (2006.01)

(56) References Cited

U.S. PATENT DOCUMENTS

| | | |
|---|---|---|
| 5,653,677 A | 8/1997 | Okada et al. |
| 2005/0272975 A1 | 12/2005 | McWeeney et al. |
| 2006/0189845 A1 | 8/2006 | Maahs et al. |
| 2012/0078050 A1 | 3/2012 | Schwartz et al. |
| 2014/0123976 A1 | 5/2014 | Mccormick et al. |
| 2014/0213850 A1 | 7/2014 | Levy et al. |
| 2014/0275772 A1 | 9/2014 | Chuda |
| 2014/0275778 A1 | 9/2014 | Gunday et al. |
| 2015/0151063 A1 | 6/2015 | Hoftman et al. |
| 2015/0257629 A1* | 9/2015 | Shahinian ............ A61B 1/0669 600/106 |
| 2016/0038001 A1 | 2/2016 | Perez-Lizano |
| 2016/0367119 A1 | 12/2016 | OuYang et al. |

* cited by examiner

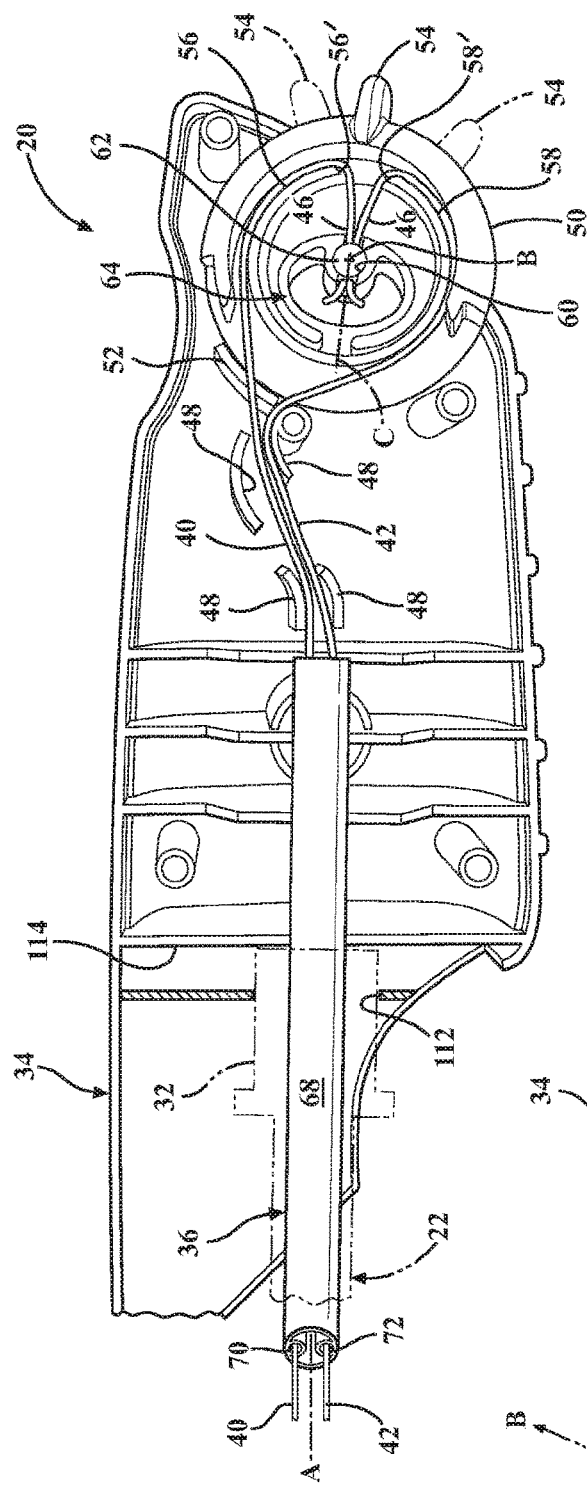
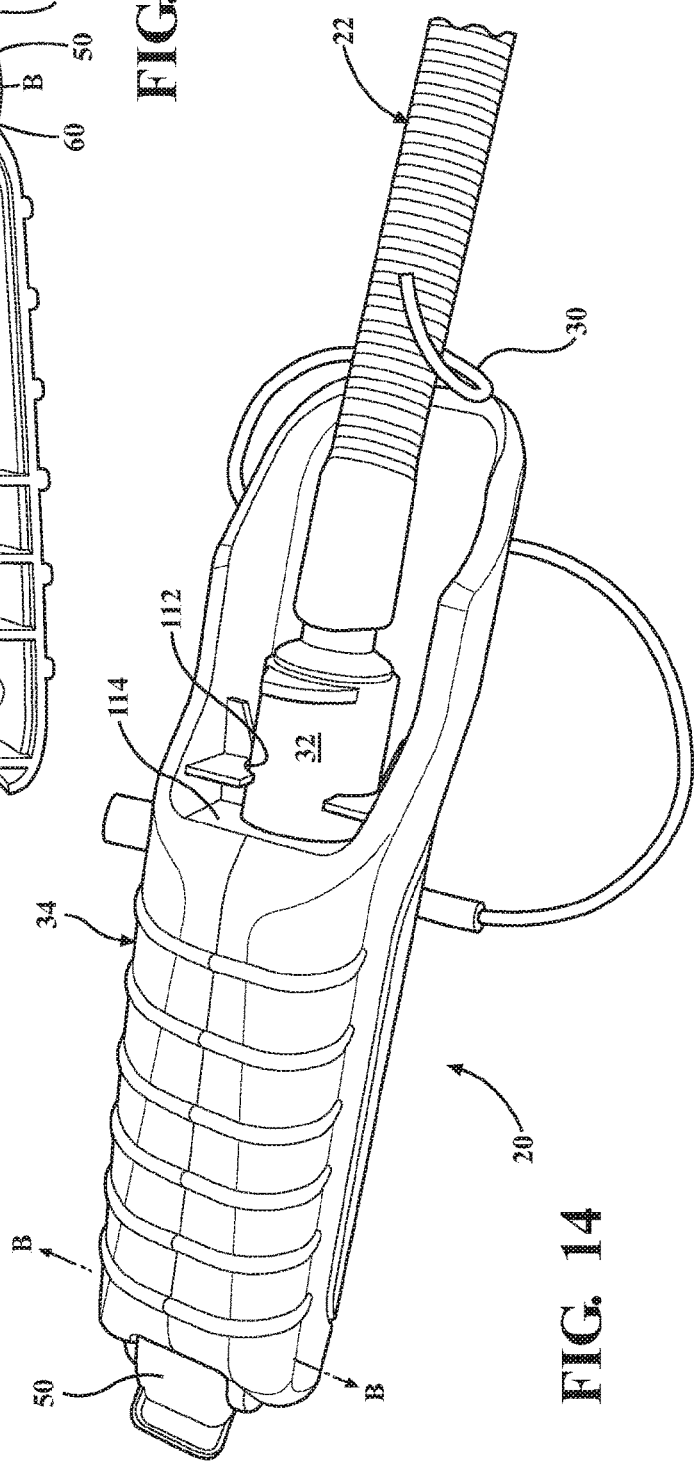
FIG. 13
FIG. 14

INTUBATION STYLET WITH VIDEO FEED

BACKGROUND OF THE INVENTION

Field of the Invention

The present disclosure relates to a manually-articulated stylet used to place an intubation device.

Description of Related Art

Endotracheal intubation is a procedure in which a flexible endotracheal (ET) tube is placed through the mouth and into the trachea to create an artificial circuit for breathing. In order to navigate the leading end of the ET tube to an optimal position in the trachea, a stylet assembly is inserted down the bore of the ET tube. One example of a stylet assembly may be seen in US Patent Publication No. 2014/0123976 to McCormick et al., published May 8, 2014 and assigned to the assignee of this present invention. The entire disclosure of US 2014/0123976 is hereby incorporated by reference and relied upon to the extent permitted by the relevant jurisdiction. A flexible distal tip of the stylet assembly protrudes through the leading end of the ET tube to serve as a steering agent that can be variably moved (typically curled or bent) by means of a remote actuator located on a handgrip at the upper end of the stylet assembly. As soon as the ET tube has reached its optimal position in the trachea, the stylet assembly is separated from the ET tube and completely withdrawn from its bore to open an air path. Thus, during the insertion process the leading end of the ET tube is carefully maneuvered through the trachea, around obstacles, with the aid of the steerable distal tip of the stylet assembly.

Intubation is frequently performed as a life-saving procedure by first responders and/or emergency room health care personnel who, on average, are much less experienced at placing intubation tubes than an anesthesiologist or an ENT (ear, nose and throat) specialist or otolaryngologist. Data suggests that over twenty million (20,000,000) intubations occur in the United States each year, and that over half (>50%) of emergency intubations are performed by first-responders in pre-hospital settings. Most first-responders in the USA have minimal intubation training and an average of only three (3) years of experience.

Studies have shown that 15 to 20 intubations are necessary to attain basic skill proficiency. Some of the medical literature is even more conservative, suggesting that the threshold for proficiency ranges from 20 to 57 consecutive, successful intubations. First responders are mandated to perform only five (5) intubations to be certified. Once in the field, on average, about two-thirds (67%) of certified paramedics will only perform one or two (1-2) intubations per year. The training standard for paramedics is also significantly less than the minimum requirement of 200 intubations for emergency medicine clinicians or over 400 for anesthesiologists. In other words, the majority of intubations are performed in life-saving settings by emergency medical workers that do not possess basic skill proficiency.

Failure rates in intubations conducted by emergency medical personnel range from 10-50%. The consequences associated with intubation failure are severe. Failed intubation can result in a wide range of ill-effects, from vocal cord paralysis to hypoxic brain injury and even death. Credible published literature attributes 180,000 deaths per year in pre-hospital emergency settings from misplaced ET tubes. And even more deaths can be attributed to misplaced intubation tubes in hospital settings.

Failure to intubate is not a problem exclusive to the first responder in an emergency/rescue setting. Difficult intubation cases present in the controlled environment of an operating room, where the rate of failure is reported to be in the range of 2-4%. Given the total number of intubations performed per year in both emergency and controlled (typically pre-operative) environments, failures occur in approximately 800,000 cases in the OR and 1,200,000 cases in emergency settings. Clinicians who routinely perform intubations attribute the primary success factor to training and experience. Not only is the intubation procedure difficult to master, but it requires regular practice to maintain proficient.

Experts in the field of stylet assembly design and manufacture have endeavored to create devices that are both easy and reliably precise to operate. This has been a challenging goal, in view of the fact that so many stylet assemblies are used in intubation procedures performed under high-stress emergency settings by under-trained first responders. One observable contributing factor to mastering difficulties with intubation placement by under-trained workers is connected to the hidden lag in steering movement after an input force has been applied to a remote actuator of the stylet assembly. This phenomenon, sometimes referred to as lost motion, is typically due to yielding or looseness of components, manufacturing tolerances, slippage or wear. The insidious problem with lost motion is that it causes the person administering the intubation procedure to inadvertently under-shoot or over-shoot steerage of the distal tip of the stylet assembly, possibly resulting in soft-tissue injury to the patient or perhaps hypoxia or worse.

Approaches to reducing these alarming failure rates have included attaching an image capture device (or video camera) onto the leading/distal tip of the ET tube or stylet assembly. The person performing the intubation procedure can see a real-time video feed (image) of the airway as the stylet advances, and in theory can better steer the ET tube to the desired position. However, data suggests that simply adding video capability to the distal tip of the stylet assembly does not produce a significant improvement in the failure rates. There is therefore a need for improved intubation devices, stylet assemblies and/or methods that reduce failure rates, which are better suited for use by paramedics and emergency department physicians who do not perform enough intubation procedures to attain (or maintain) skill proficiency.

BRIEF SUMMARY OF THE INVENTION

According to a first aspect of this invention, a manually articulated stylet assembly is provided for facilitating placement of an intubation device in a patient. The assembly comprises at least one flexible motion transmitting element having a controlled end and a controlling end. A remote actuator is supported on a handle of the stylet assembly for movement toward and away from at least one actuated position. The remote actuator includes an anchor point that connects with the controlling end of the motion transmitting element. A steering shaft extends from the handle. The steering shaft has an elongated tubular main stem that defines a centerline along its length. A flexible end-piece adjoins the main stem at a transition and extends longitudinally along the centerline to a distal tip. The motion transmitting element is routed along the steering shaft with its controlled end connected to the distal tip of the end-piece such that movement of the remote actuator causes a corresponding movement at the far-off distal tip. A recessed lens pocket is formed in the steering shaft adjacent the transition and spaced from the distal tip. The lens pocket is laterally offset from the centerline for partially housing an image capture device in a forward-pointing direction so that its field of view is oriented to capture movement of the distal tip in response to actuation of the remote actuator.

By locating the recessed lens pocket away from the distal tip, near the transition between main stem and end-piece, the image capture device will capture an image of the distal tip within its field of view. The person performing the intubation procedure will see real-time movement of the distal tip and thus better steer the ET tube through the trachea. As a result, paramedics and emergency department physicians under-trained and/or out-of-practice in intubation procedures will be more likely to achieve successful intubations.

According to a second aspect of this invention, a manually articulated stylet assembly is provided for facilitating placement of an intubation device in a patient. The assembly comprises at least one flexible motion transmitting element that has a controlled end and a controlling end. The stylet assembly also includes a handle. The handle has a journal that defines a pivot axis. A remote actuator is supported in the journal for movement about the pivot axis toward and away from at least one actuated position. The remote actuator, in turn, includes at least one track for supporting variable lengths of the motion transmitting element as the remote actuator is rotated about the pivot axis. The remote actuator also includes an anchor point that connects the controlling end of the motion transmitting element. A steering shaft extends from the handle. The steering shaft has an elongated main stem that defines a centerline along its length. The motion transmitting element extends along the length of the steering shaft. A flexible end-piece extends longitudinally from the main stem along the centerline to a distal tip. The controlled end of the motion transmitting element is connected to the distal tip of the end-piece. Within the remote actuator, a biasing member is disposed between the anchor point and the track.

By locating a biasing member within the remote actuator, slack in the motion transmitting element will be taken-up, thus eliminating or at least substantially reducing the occurrence of lost motion. As a direct result, the person performing the intubation procedure will be in better control of the distal tip via the remote actuator. Better control means that practitioners, and especially paramedics and emergency department physicians who do not perform enough intubation procedures to attain (or maintain) skill proficiency, will be less likely to experience an intubation failure.

BRIEF DESCRIPTION OF THE SEVERAL VIEWS OF THE DRAWINGS

These and other features and advantages of the present invention will become more readily appreciated when considered in connection with the following detailed description and appended drawings, wherein:

FIG. 13 shows the interior cavity region of the handle and the journal therein supporting the remote actuator for reciprocating movement about a pivot axis; and FIG. 14 is a fragmentary bottom perspective view of the handle including a collar portion of an ET tube frictionally fit in a collar seat located in the handle.

DETAILED DESCRIPTION OF THE INVENTION

Figure 1:
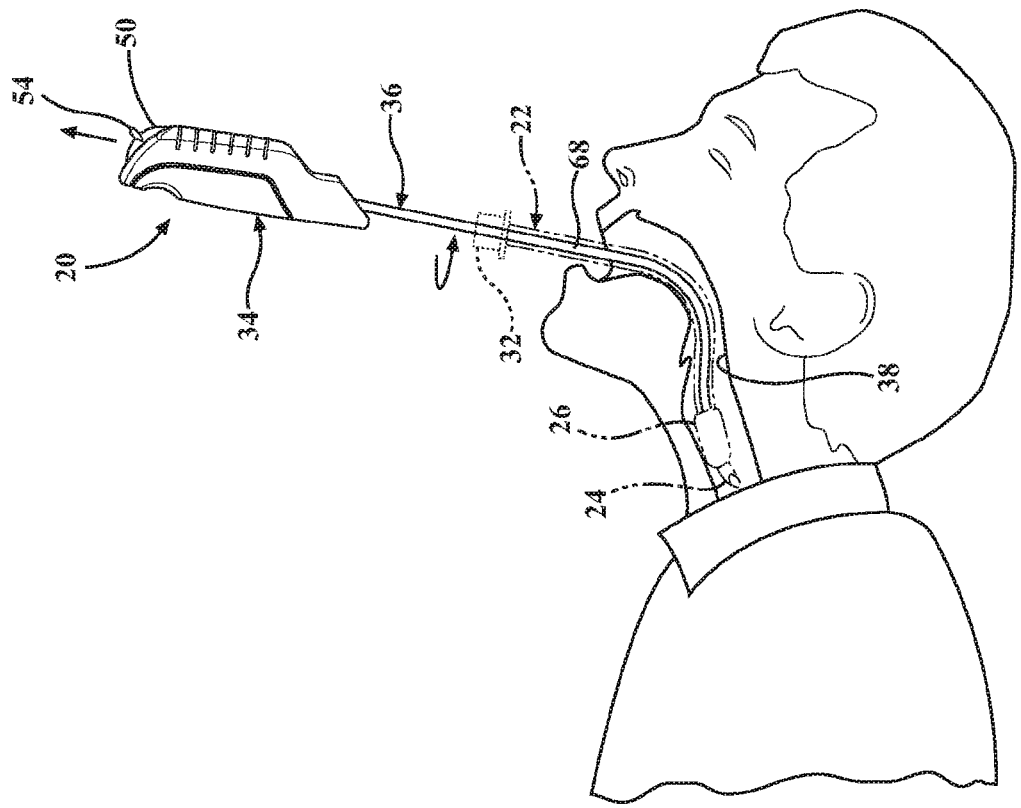
FIG. 1 is a simplified view of an intubation process with a patient depicted in partial section along the median or sagittal plane, with a stylet assembly shown in solid and a coupled endotracheal (ET) tube in phantom, and wherein the leading end of the ET tube is just passing the epiglottis.

Example embodiments will now be described more fully with reference to the accompanying drawings. The illustrations depict exemplary embodiments of the invention in various contexts so that those who are skilled in the art can more readily comprehend its construction and use. Naturally, throughout the following description specific details may be referenced in the context of the exemplary embodiments, when in fact the specific details may be optional and/or may be configured in alternative forms to achieve comparable results.

A manually articulated stylet assembly is generally shown at 20 throughout the figures. The stylet assembly 20 is adapted to facilitate placement of an intubation device, such as an endotracheal (ET) tube 22, in a patient. The ET tube 22 may be of any commercially-available variety, having a flexible hollow conduit with a leading end 24 that is typically angled. An inflatable cuff 26 is located along the conduit near the leading end 24. Inflation of the balloon-like cuff 26 is controlled through a pilot tube 30 (FIG. 14). A generally cylindrical collar connector 32 caps the rear or upper end of the ET tube 22. The purpose of the collar connector 32 is to form a temporary, easily released attachment with the stylet assembly 20, as will be described in detail below.

Figure 2:
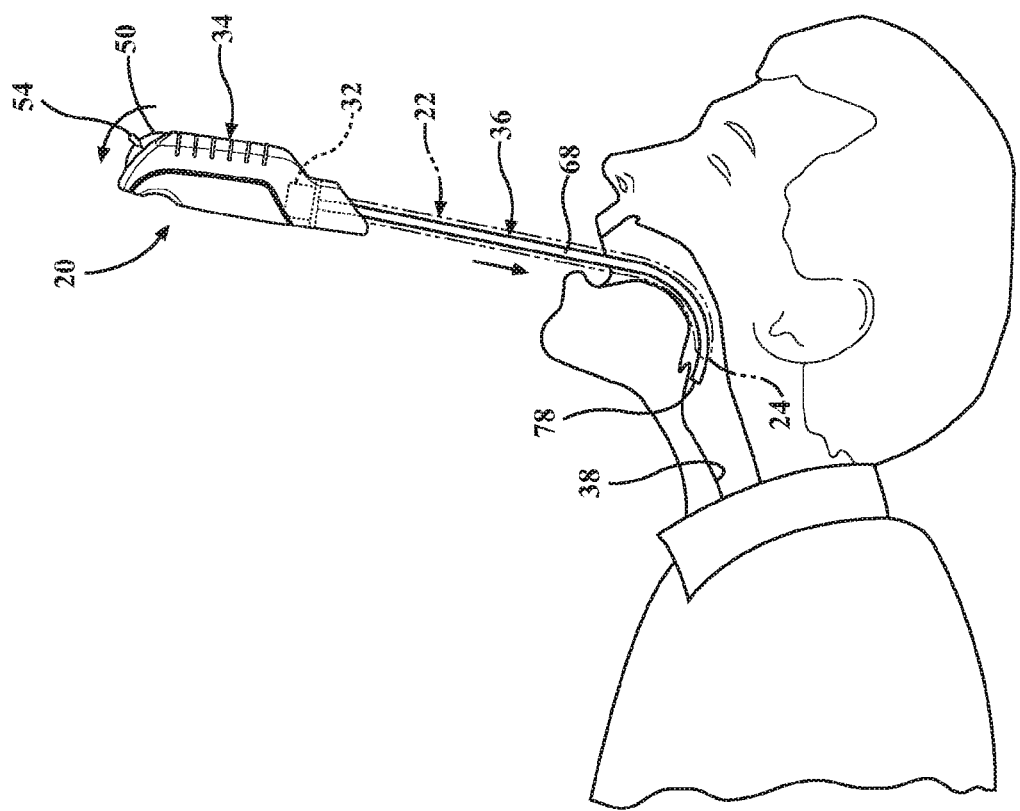
FIG. 2 is a view as in FIG. 1 but wherein the ET tube has reached an optimal position and the stylet assembly is being withdrawn.
Figure 3:
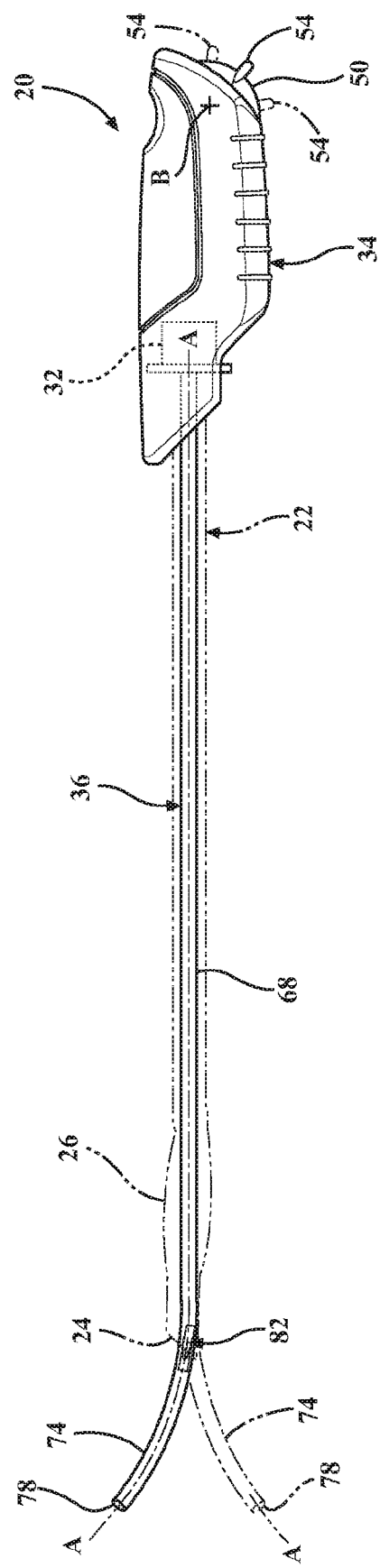
FIG. 3 is a side elevation of a stylet assembly according to one exemplary embodiment of the invention, with its distal tip shown downwardly flexed in phantom, and with an ET tube also shown in phantom.
Figure 4:
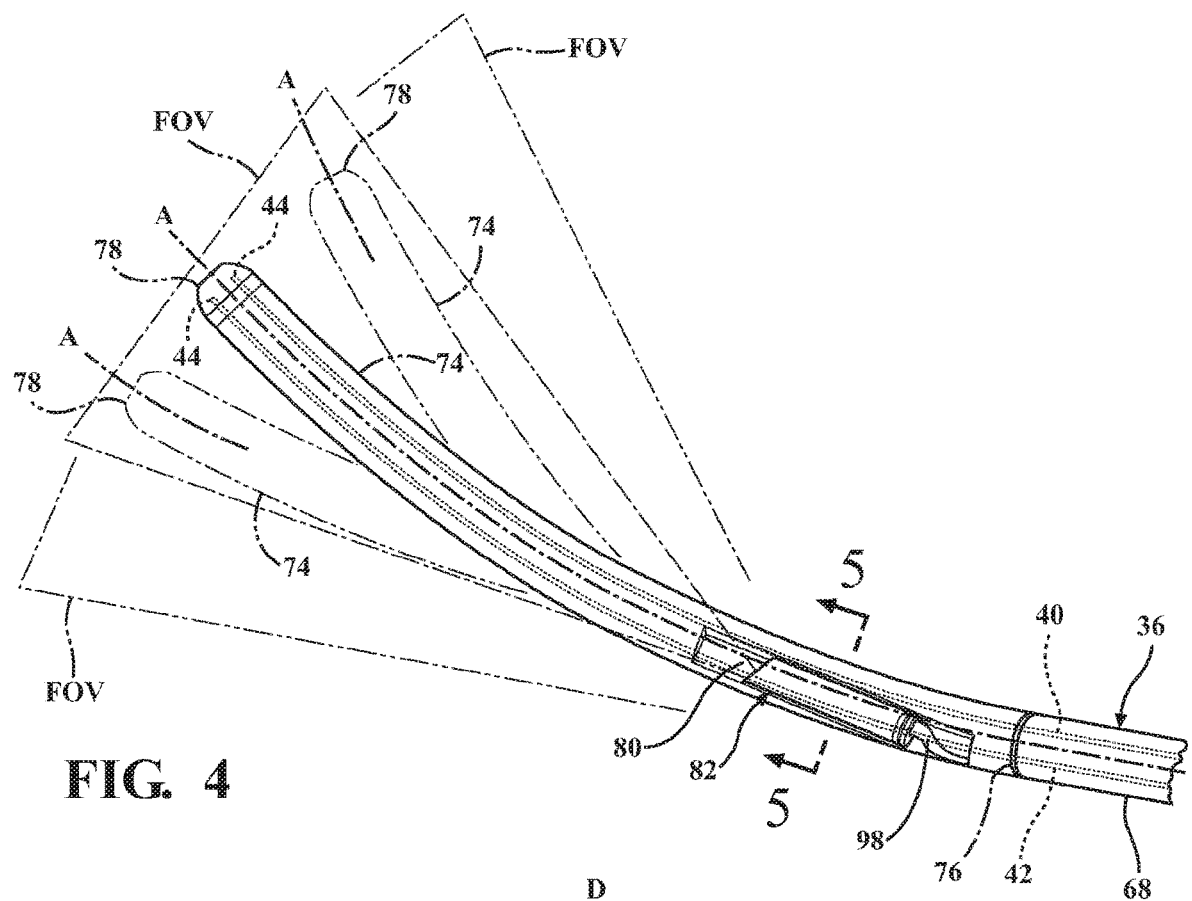
FIG. 4 is a fragmentary view of the stylet assembly showing its distal tip in various articulated positions and the corresponding changes in camera field of view as a function of distal tip movement.
Figure 5:
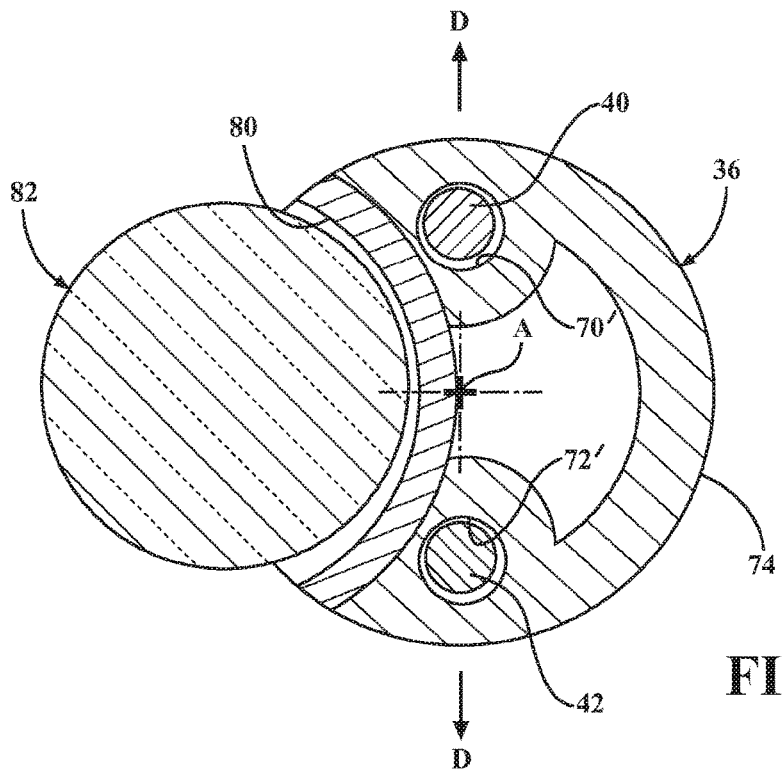
FIG. 5 is a cross-section taken generally along lines 5-5 in FIG. 4 to depict how the image capture device is partially housed within the recessed lens pocket in one exemplary embodiment of the invention.

The stylet assembly 20 is shown in FIGS. 1-3 including a handle 34 and a steering shaft 36. Throughout the figures, the steering shaft 36 is depicted in the form of a hollow tubular member. However, in some contemplated embodiments the steering shaft 36 is not tubular but rather flat tape-like or perhaps I-shaped in cross-section. Many shapes are possible. The steering shaft 36 extends from the handle 34 along a centerline A. The centerline A is not linear, but rather follows the length of the long, narrow steering shaft 36 as it curves and flexes like a snaking-device within the hollow ET tube 22. The steering shaft 36 is sized to be slid down the bore or conduit of the ET tube 22 during an intubation procedure like that depicted in FIGS. 1-2 and also in FIGS. 8-10. During the insertion procedure, the steering shaft 36 is manipulated to help guide the leading end 24 of the ET tube 22 through obstacles and toward the proper destination in the patient's trachea 38. As soon as the ET tube 22 reaches the intended location in the trachea 38 (FIG. 2), the stylet assembly 20 is wholly withdrawn by carefully disconnecting the handle 34 from the collar connector 32 (described more fully below) and then sliding the steering shaft 36 out from the conduit-like bore of the ET tube 22. At this point, the stylet assembly 20 is either discarded or cleaned for re-use.

The maneuverable qualities of the steering shaft 36 are achieved via at least one, but more typically two, flexible motion transmitting elements 40, 42 extending along the length of the steering shaft 36. In the common configuration, one of the motion transmitting elements can be designated an upper motion transmitting element 40 and the other a lower motion transmitting element 42. Naturally, the upper and lower designations are somewhat arbitrary but correlate with the orientation of the assembly 20 when gripped and used in the common way. The upper 40 and lower 42 motion transmitting elements can be made of any suitable material capable of transmitting forces, including metallic wires, cords, cables, tapes and the like.

Each motion transmitting element 40, 42 has a controlled end 44 and a controlling end 46. Forces applied by the user at the controlling ends 46 are transmitted along the lengths of the respective motion transmitting elements 40, 42 resulting in a corresponding movement at the controlled ends 44. In some contemplated embodiments, the motion transmitting element 40, 42 can comprise a single force transmitter capable of transmitting both tensile and compressive forces—i.e., a push-pull system. In other embodiments, like those shown in the illustrated examples, the motion transmitting element 40, 42 is composed of two separate tensile-only force transmitters—i.e., a pull-pull system. In the latter case, the exemplary embodiments contemplate two separate and distinct wires or cables 40, 42. However, with minor modifications, a motion transmitting element in the form of a single continuous loop, suitably anchored to achieve functional equivalents of the controlled 44 and controlling 46 ends, could be readily envisioned by those of ordinary skill in this art.

The handle 34 has a hollow interior cavity (FIG. 13) in which one or more guides 48 are disposed to establish a guide path for the upper 40 and lower 42 motion transmitting elements in-between the steering shaft 36 and a remote actuator 50. The remote actuator 50 is supported on the handle 34 for movement toward and away from at least one actuated position, through which movements the user variably applies forces to the controlling ends 46 of the motion transmitting elements 40,42 to achieve corresponding movements at the far-away controlled ends 44. The remote actuator 50 can take many different forms. In some contemplated embodiments, the remote actuator 50 is configured to slide back and forth in a linear track (not shown). In other contemplated embodiments, the remote actuator 50 is configured to reciprocate in and out like a push-button (not shown). In still other contemplated embodiments, the remote actuator 50 is configured for movement like the trigger of a spray bottle or a squeeze-lever (not shown). Many different possibilities exist. However, in the illustrated examples the remote actuator 50 is configured to oscillate arcuately about a pivot axis B.

The interior cavity of the handle 34 includes a journal 52 (FIG. 13) that supports the remote actuator 50 for pivotal movement like a simple bearing or bushing. In the illustrated examples, the remote actuator 50 is designed to partially reside within the interior cavity of the handle 34 supported by the journal 52. The remote actuator 50 has a generally circular interface that mates with the journal 52 in rotational sliding contact. In this manner, both the interface of the remote actuator 50 and the journal 52 define the pivot axis B. Although the pivot axis B could be oriented in almost any direction, the accompanying illustrations show the pivot axis B traversing horizontally through the handle 34, generally perpendicular to the centerline A of the steering shaft 36.

Figure 11:
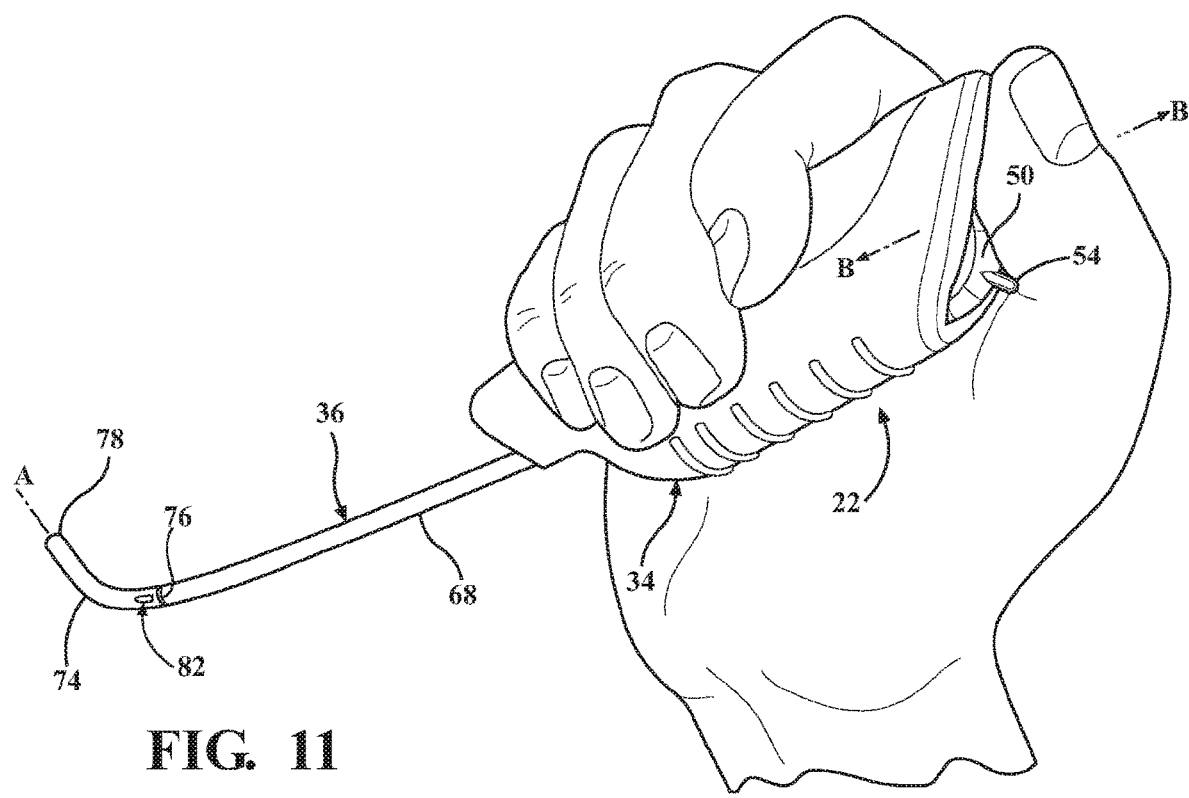
FIG. 11 is a perspective view of the stylet assembly of FIG. 3, showing the typical grip in the user's right hand with thumb positioned on the remote actuator.

A portion of the wheel-like remote actuator 50 is exposed outside the handle 34 so that the person administering the intubation procedure can readily access the remote actuator 50 with one or more fingers. To increase tactile responsiveness, the remote actuator 50 may include a thumb tab 54 protruding from the exposed portion, as seen in FIGS. 3 and 13. That is to say, the thumb tab 54 is accessible outside of the handle 34. This configuration allows a user gripping the handle 34 with a "ice pick" style hold to manipulate the remote actuator 50 with comfortable up and down movements of the thumb as shown in FIG. 11.

Figure 12:
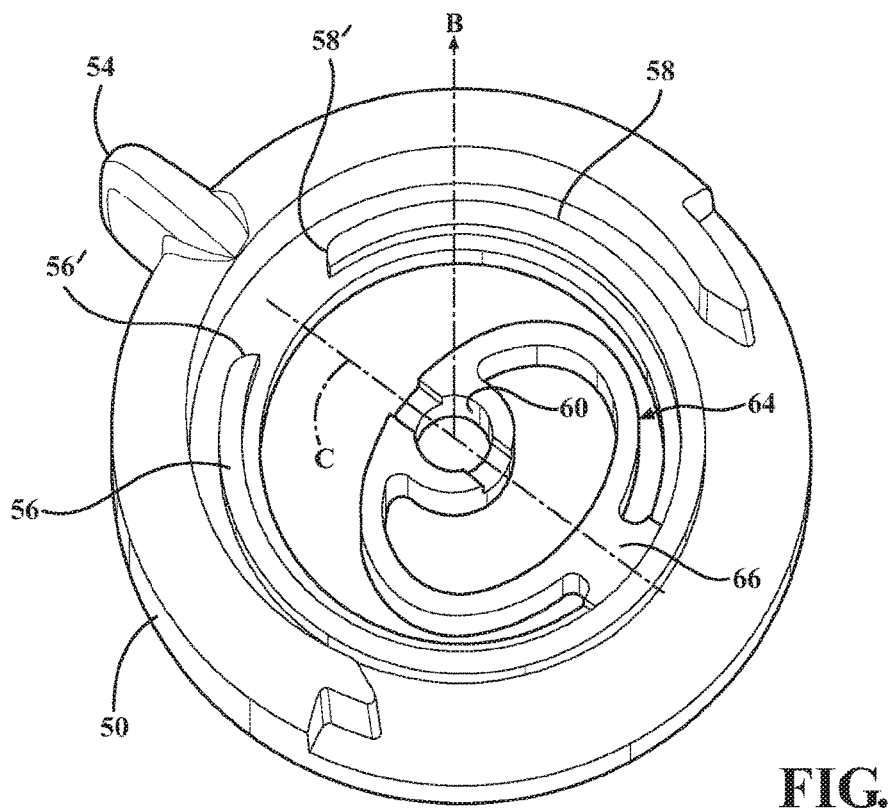
FIG. 12 is a perspective view of a remote actuator having tracks for supporting variable lengths of the motion transmitting element and a biasing member disposed between the tracks and an anchor point for the motion transmitting element.

FIGS. 12 and 13 show the remote actuator 50 in some detail, according to one possible embodiment. The remote actuator 50 in these examples includes upper 56 and lower 58 tracks for respectively supporting variable lengths of the upper 40 and lower 42 motion transmitting elements. As the remote actuator 50 is rotated about the pivot axis B, exposed sections of the upper 40 and lower 42 motion transmitting elements will wind and un-wind on these tracks 56, 58 somewhat akin to the action of a cable wrapped around a cam or a belt around a pulley. In the illustrated examples, the upper 56 and lower 58 tracks are semi-circular and generally concentrically co-located about the pivot axis B. However, the upper 56 and lower 58 tracks could be asymmetrical and/or designed to provide non-linear camming effects if desired. In some alternative embodiments envisioned but not illustrated, a single track could be used by both upper 40 and lower 42 motion transmitting elements. Or, a single track could be used by a single motion transmitting element. Indeed, many variations are possible in the matter of the tracks 56, 58.

The remote actuator 50 has an anchor point 60 that connects with the controlling ends 46 of the upper 40 and lower 42 motion transmitting elements. The anchor point 60 generally coincides with the pivot axis B, however the two are expected to shift out of phase as tension in the motion transmitting elements 40, 42 fluctuates. In FIGS. 12 and 13, the anchor point 60 takes the form of a socket adapted to receive a cylindrical lug 62 crimped to both motion transmitting elements 40, 42. The common points at which the upper 40 and lower 42 motion transmitting elements attach to the lug 62 are the respective controlling ends 46 in this embodiment. The tracks 56, 58 are generally concentrically spaced apart from the anchor point 60. Each track 56, 58 has a driving edge 56', 58', respectively, about which the motion transmitting elements 40, 42 wrap. The driving edges 56', 58' are separated from one another to form a small gap through which both motion transmitting elements 40, 42 have clearance to pass through to the anchor point 60. The radial distance between the anchor point 60 and the driving edges 56', 58' is, in effect, a moment arm. Rotation of the remote actuator 50 applies a force (load) to the respective motion transmitting elements 40, 42 through the leverage created between the offset driving edges 56', 58' relative to the anchor point 60. In some respects, it could be viewed that the actual effective controlling ends 46 of the motion transmitting elements 40, 42 are at the driving edges 56', 58' rather than the anchor point 60. Such technical parsing is not, however, necessarily germane to the understanding of this invention. Instead, the core teaching here is that the remote actuator 50 concurrently drives the controlling ends 46 of the motion transmitting elements 40, 42 as the remote actuator 50 is rotated about the pivot axis B.

One of the unique aspects of this invention is the incorporation of a biasing member 64 between the anchor point 60 and the tracks 56, 58. The purpose of the biasing member 64 is to maintain a pre-tension on the motion transmitting elements 40, 42 at all times. By maintaining pre-tension, the opportunity for lost motion in the system is substantially reduced and/or eliminated. The biasing member 64 can take many different forms and yet still maintain an even tensile force in the motion transmitting elements 40, 42. Some contemplated forms include springs, coils, pneumatic devices and resilient materials, to name but a few. In the depicted embodiment, however, the biasing member 64 takes a generally elliptical configuration as shown in FIGS. 12 and 13. Effectively, the elliptical biasing member 64 is of the double-leaf spring category in which two bowed arms in mirror fashion connect (at 66) to the remote actuator 50, and the connection point 66 is functionally between the tracks 56, 58 and the anchor point 60. Preferably, but not necessarily, the connection point 66 for the elliptical biasing member 64 is positioned strategically along an imaginary radial C passing through both the anchor point 60 and the driving edges 56', 58' of the respective tracks 56, 58. As clearly seen in FIG. 12, the connection point 66 for the elliptical biasing member 64 is diametrically opposite the driving edges 56', 58'. Alternatively (not shown), the connection point 66 for the elliptical biasing member 64 could be diametrically-opposite to that depicted, just inside the gap between the driving edges 56', 58'. By locating the connection point 66 of the elliptical biasing member 64 along an imaginary radial C passing through both the anchor point 60 and the driving edges 56', 58', relatively even tensile loading can be maintained on the motion transmitting elements 40, 42 throughout the range of operating motions and conditions. Such placement of the connection point 66 helps maintain the anchor point 60 at an equal distance from each driving edge 56', 58' even as the anchor point 60 moves under varying tensile loads. That is to say, the double-leaf spring configuration of the biasing member 64, combined with the strategic location of the connection point 66 along the imaginary radial C, constrains travel of the anchor point 60 along that same imaginary radial C. By maintaining equal distance between anchor point 60 and each driving edge 56', 58', while the anchor point 60 shifts under varying loads, the controlled ends 44 of the motion transmitting elements 40, 42 will not be affected. And the undesirable effects of lost motion are substantially subdued if not eliminated altogether. In this manner, a person performing an intubation procedure is better able to accurately control the steering shaft 36 and thus placement of an ET tube 22.

Turning now to FIGS. 3-6, the steering shaft 36 will be described in further detail. As previously mentioned, the centerline A follows the steering shaft 36 along its length. A majority of that length is composed of an elongated main stem 68 that attaches to the handle 34 within its interior cavity (FIG. 13). The main stem 68 is generally straight, and relatively stiff yet still able to be flexed. In the examples shown, the main stem 68 is tubular and has a generally constant circular outside diameter along its full longitudinal length. However, as mentioned above the steering shaft 36, and by extension therefore also the main stem 68, can have an open construction such as a flat tape-like shape or I-shape or back-to-back C-shape (⊃ ⊂) to name but a few of the many possibilities. As show in the exemplary depictions, main stem 68 may be a simple hollow tube within which the upper 40 and lower 42 motion transmitting elements are loosely contained, or the main stem 68 can be partitioned (e.g., Θ) longitudinally for form respective upper 70 and lower 72 lumens (i.e., conduits) to establish respective sliding guide paths for the upper 40 and lower 42 motion transmitting elements. The upper 70 and lower 72 lumens can be open channels (as could be the case when the main stem 68 has an open construction such as an I-shape or back-to-back C-shape) or fully-enclosed conduit-like sheaths or passages. The illustrated embodiment shows fully-enclosed conduit-like upper 70 and lower 72 lumens in FIG. 13. In this example, the upper 70 and lower 72 lumens are diametrically opposed from one another within an articulation plane, as indicated by a vertical line D shown in FIGS. 5 and 6. The articulation plane D passes through the centerline A, even as the centerline A and steering shaft 36 are maneuvered during intubation. It can also be seen that the articulation plane D perpendicularly bisects the pivot axis B of the remote actuator 50.

The steering shaft 36 also has a flexible end-piece 74 that adjoins the main stem 68 at a transition 76. The end-piece 74 has a generally constant circular outside diameter that may be substantially equal to the outside diameter of the main stem 68. In this manner, the end-piece 74 extends from the main stem 68 along the centerline A, terminating at a distal tip 78. Unlike the somewhat stiff main stem 68, the end-piece 74 is highly flexible and resilient. The transition 76 is defined as the junction between the relatively stiff main stem 68 and highly flexible end-piece 74. Because the flexibility of the end-piece 74 can be accomplished in a variety of ways, the transition 76 can likewise take many different forms. In some cases, the end-piece 74 is formed by molding or machining slits in its body similar to those depicted, for example, in the aforementioned US Patent Publication No. US 2014/0123976. In such cases, the transition 76 may be the approximate location where the slits begin. In some situations, the end-piece 74 may have a pre-set angled or curve relative to the main stem 68. The transition 76 is these situations will be the region where the slope of the centerline A changes. In the present example, the end-piece 74 does not have slits, but instead achieves flexibility through its material composition which is dissimilar to that of the main stem 68. In this case, the end-piece 74 could be separately fabricated (as a loose piece) and then joined or fused to the end of the main stem 68. The transition 76 would thus be the bond joint. In another contemplated variation, manufacturing techniques are employed to co-form the main stem 68 and end-piece 74 albeit of dissimilar material compositions. In one example, an extrusion process is used to form the main stem 68. Once a desired length of main stem 68 is achieved, on-the-fly, steps are taken to alter the composition of the extruded material so that its resiliency is highly enhanced whereupon continued extrusion forms the end-piece 74 as an integral member. In this latter case, the transition 76 is the span or region of material bridging the relatively stiff main stem 68 and the highly flexible end-piece 74.

Figure 6:
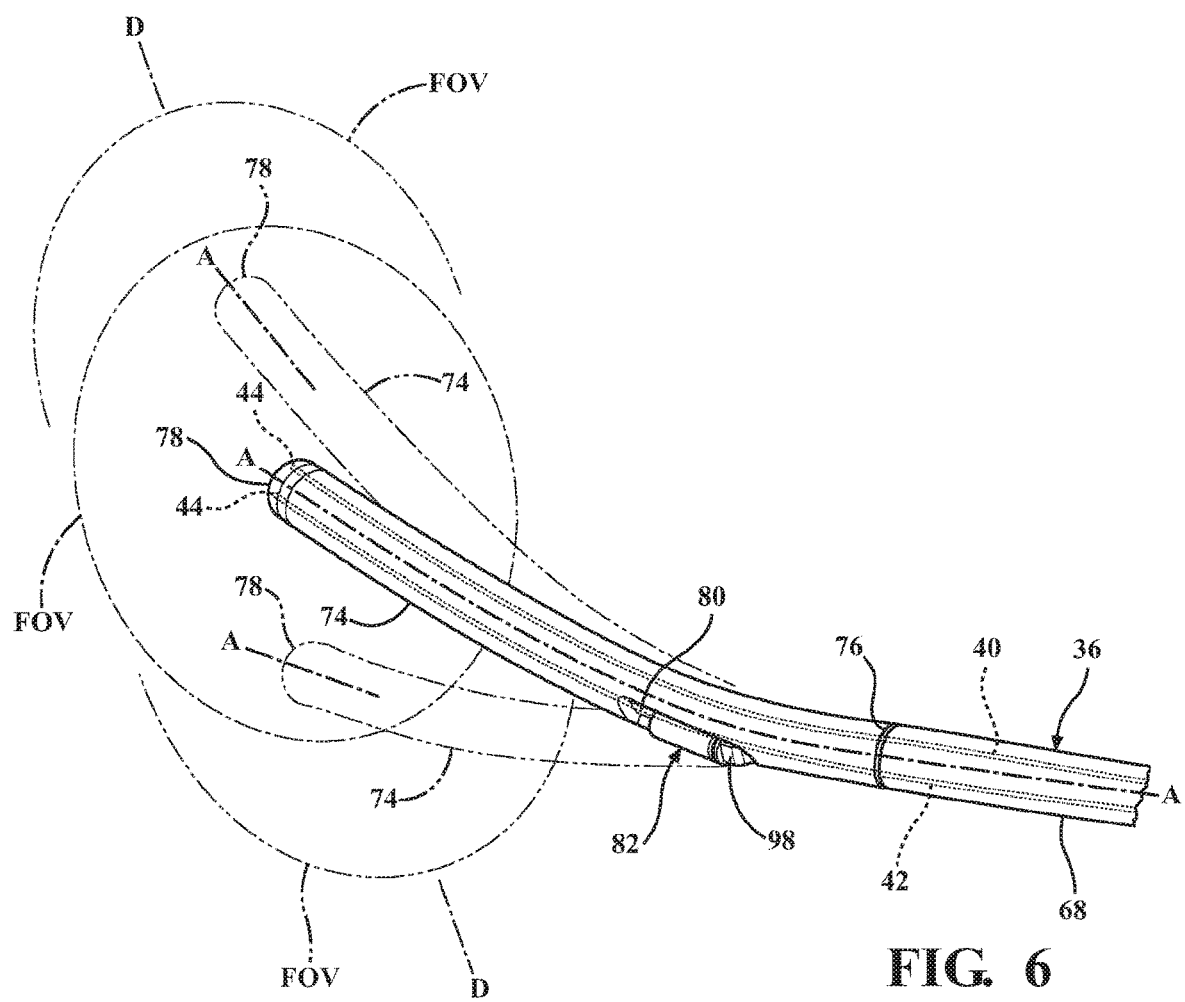
FIG. 6 is a perspective view of the distal tip having been steered to several different positions and the corresponding changes in camera field of view as a function of distal tip movement.

In the illustrated examples, the end-piece 74 has a pre-set curvature laying within the articulation plane D, as best shown in FIG. 6. The pre-set curvature can be associated with a resting position in which a slight upward curvature is maintained even when no force is exerted on the remote actuator 50. The end-piece 74 may be formed with upper 70' and lower 72' lumen extensions that align with (i.e., continue) the respective the upper 70 and lower 72 lumens of the main stem 68 to establish continuous sliding guide paths for the upper 40 and lower 42 motion transmitting elements within the articulation plane D. As illustrated by the phantom image overlays in FIGS. 4 and 6, the end-piece 74 can be moved via the remote actuator 50 from its resting position to either a positive incline position or a negative incline position. Alternative embodiments are contemplated wherein the upper 70 and lower 72 lumens are omitted partially or entirely from the main stem 68, however the upper 70' and lower 72' lumen extensions remain in the end-piece 74. In this manner, portions of the upper 40 and lower 42 motion transmitting elements that extend through the end-piece 74 are maintained within the articulation plane D, even though portions of the motion transmitting elements 40, 42 within the main stem 68 are unconstrained. Within the end-piece 74, the controlled ends 44 of the upper 40 and lower 42 motion transmitting elements are directly fixedly connected to the distal tip 78. This may be accomplished in a variety of ways. According to one method, the distal tip 78 is formed by small plug-like cap that is fixed to the free end of the end-piece 74. The cap can thus preform the dual function of anchoring the controlled ends 44 of the upper 40 and lower 42 motion transmitting elements and also closing/sealing the end-piece 74. The distal tip 78 preferably has a smoothly-domed end to discourage snagging on tissue.

Thus, it will be appreciated that the motion transmitting elements 40, 42 extend, functionally, between the distal tip 78 and the remote actuator 50. The controlling ends 46 are attached to the remote actuator and the controlled ends 44 are attached to the distal tip 78. When an operator moves the remote actuator 50, such as with an upward or downward motion of the thumb, a corresponding movement at the distal tip 76 is induced. In this manner, the person performing an intubation can, with a single hand, hold the handle 34 and cause the distal tip 78 to flex up and down within the articulation plane D. And of course with the same one hand the operator can twist the entire stylet assembly 20 as well as push and pull to help maneuver an ET tube into position in a patient's trachea.

Turning to FIGS. 4-7, another unique feature of the stylet assembly 20 will be described. As mentioned previously, approaches to reducing intubation failure rates particularly among under-trained members of the first responder community have included attaching an image capture device (or video camera) onto the leading end of the ET tube or stylet assembly. Attaching an image capture device provides the person performing the intubation procedure with a real-time video feed (live moving image) of the airway 38. In practice, however, only minimal improvements in intubation failure rates were observed with the addition of live video feed. The present invention addresses this shortcoming by providing a lens pocket 80 in the steering shaft 36 adjacent the transition 76. By spacing the lens pocket 80 away from the distal tip 78, substantial improvement in intubation success rates, particularly among under-trained users, has been observed. The lens pocket 80 is shown in the illustrated examples to be a scalloped region inset to the tubular body of the steering shaft 36. Preferably, the lens pocket 80 is laterally offset from the centerline A. More preferably still, the lens pocket 80 is laterally offset from articulation plane D, in either the 3 o'clock or 9 o'clock positions to avoid interference with any of the lumens 70, 70', 72, 72'. An advantage of this latter example enables the lens pocket 80 to be generally equally spaced between the upper 40 and lower 42 motion transmitting elements, and thereby mitigate or avoid altogether unequal influencing affects when the motion transmitting elements 40, 42 are actuated. The lens pocket 80 can be located entirely within the main stem 68, or entirely within the end-piece 74, or can intersect the transition 76 itself. In any case, however, the lens pocket 80 is very closely positioned relative to the transition 76, relatively far-away from the distal tip 78. For reasons to be detailed below, there is some advantage to locating the lens pocket 80 entirely within the end-piece 74 directly adjacent the transition 76.

Figure 7:
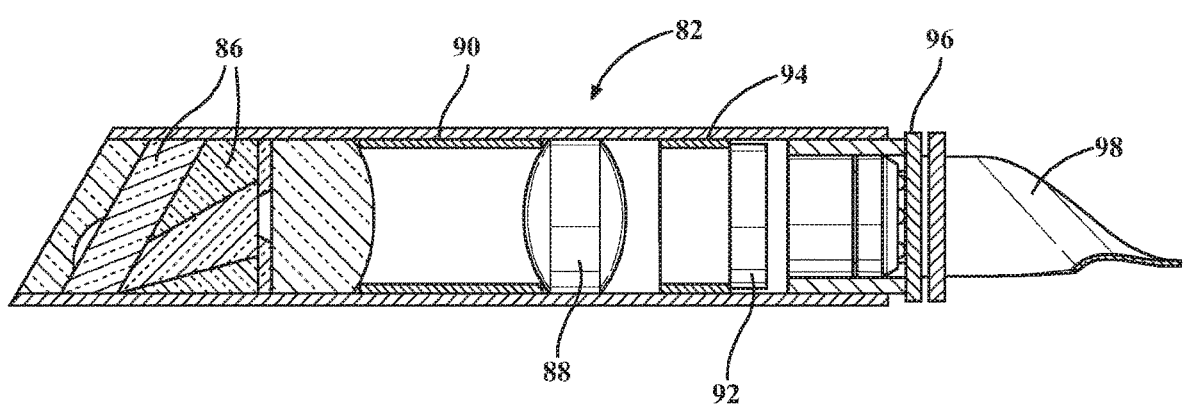
FIG. 7 is a longitudinal cross-section through an image capture device according to one contemplated embodiment of this invention.

An image capture device, generally indicated at 82, is disposed in the lens pocket 80. The image capture device 82 is capable of producing, or being used to produce, a live video feed transmissible by wire or wireless signal to a remote monitor 84 such as a general-purpose computer screen or tablet or a special-purpose display screen. The term "image capture device" is intended to be broadly construed to include any and all suitable forms of image capture technology. In this context, the image capture device 82 could in fact be only an optical lens or set of lenses, or could be a full compact digital camera assembly. The latter case of a full compact digital camera assembly is depicted in FIG. 7 as an example. Image capture device is not necessarily limited to capture of light in the visible spectrum. Some other contemplated forms of image capture device 82 might include image capture based on radio magnetic waves outside the visible spectrum as well as using sound reflection or the like. Indeed, the invention is directed toward the location of the image capture device 82 more so than its underlying image capture technology.

The image capture device 82 has a field of view FOV which typically, but not necessarily, emanates in a cone-shape. The lens pocket 80 partially houses the image capture device 82 in a forward-pointing direction so that the field of view FOV captures movement of the distal tip 78 in response to actuation of the remote actuator 50. That is, the field of view FOV is directed toward the distal tip 78. Due to the strategic location of the lens pocket 80 adjacent the transition 76, the cone-shaped field of view FOV will capture most or all of the steerable end-piece 74. As a result, the live video feed image produced by the image capture device 82 will include the end-piece 74. User inputs at the remote actuator 50 will be observable in real-time via the image appearing on the remote monitor 84.

Figure 8:
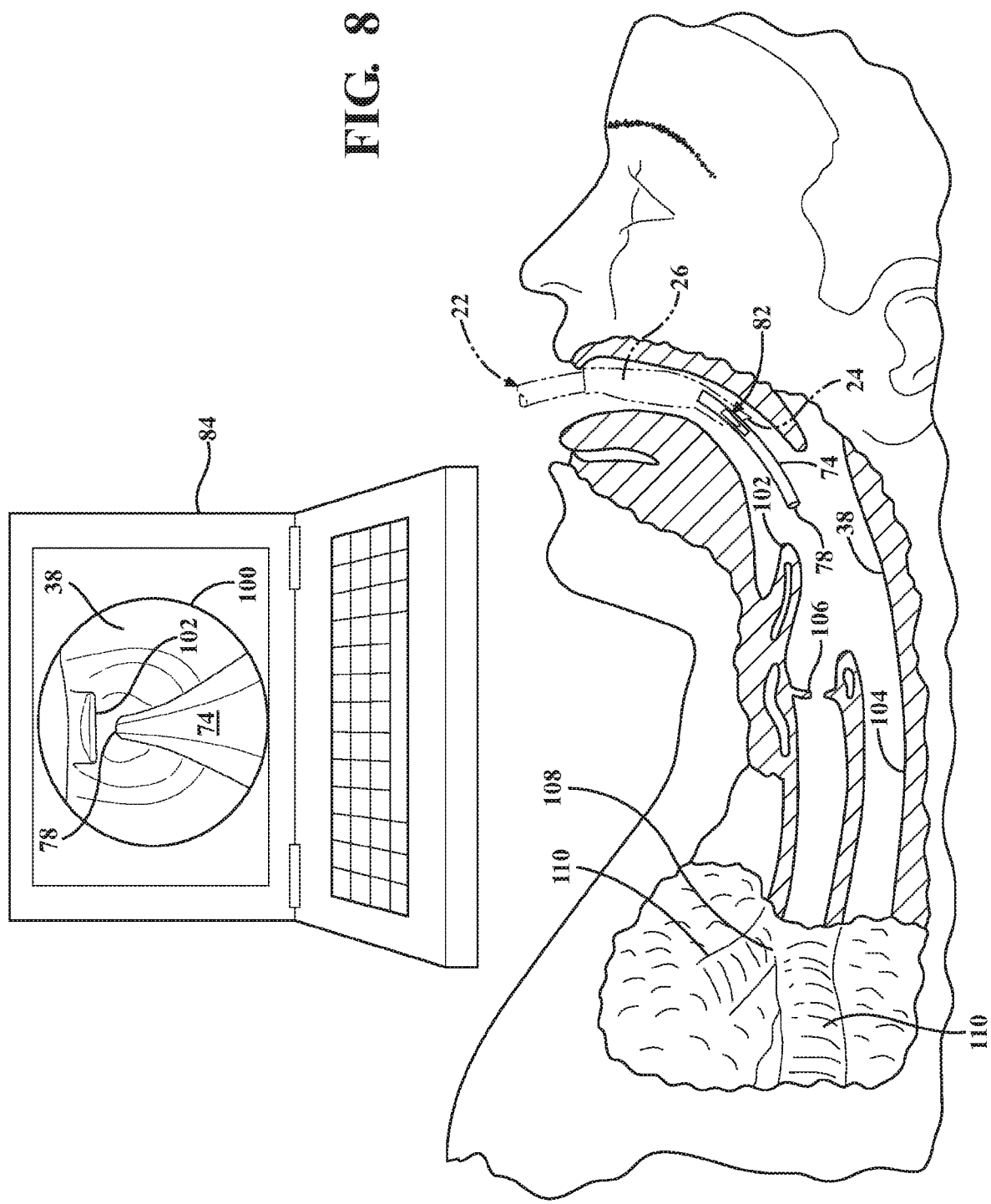
FIG. 8 is a highly-simplified view of an intubation process with a patient depicted in section along the sagittal plane, the leading end of an ET tube and stylet assembly shown approaching the patient's epiglottis, and an exemplary view from the video camera projected onto a nearby monitor or screen.
Figure 9:
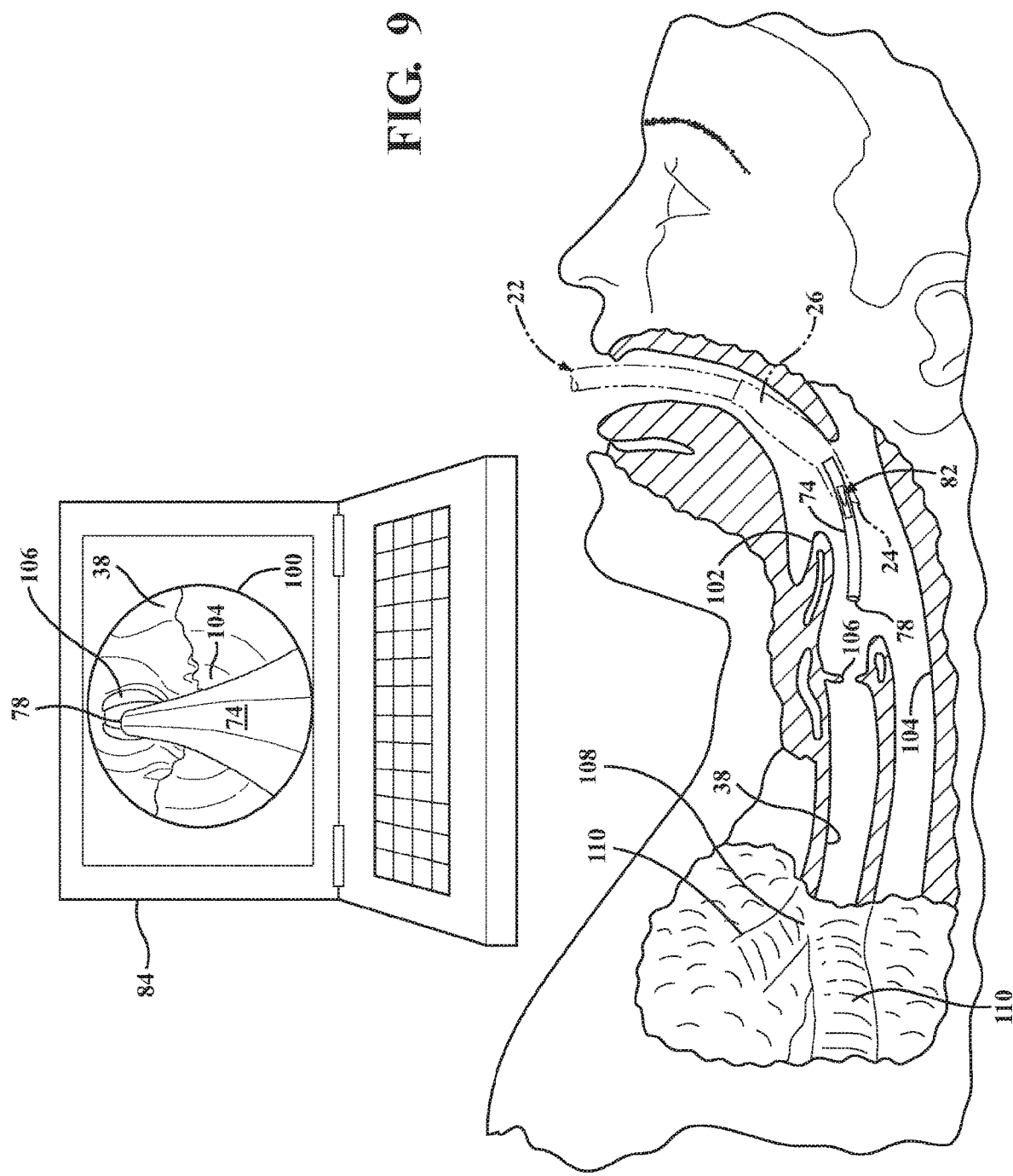
FIG. 9 is a view as in FIG. 8 where the leading end of the ET tube and stylet assembly are approaching the patient's vocal cords, and an exemplary view from the video camera projected onto a nearby monitor or screen.
Figure 10:
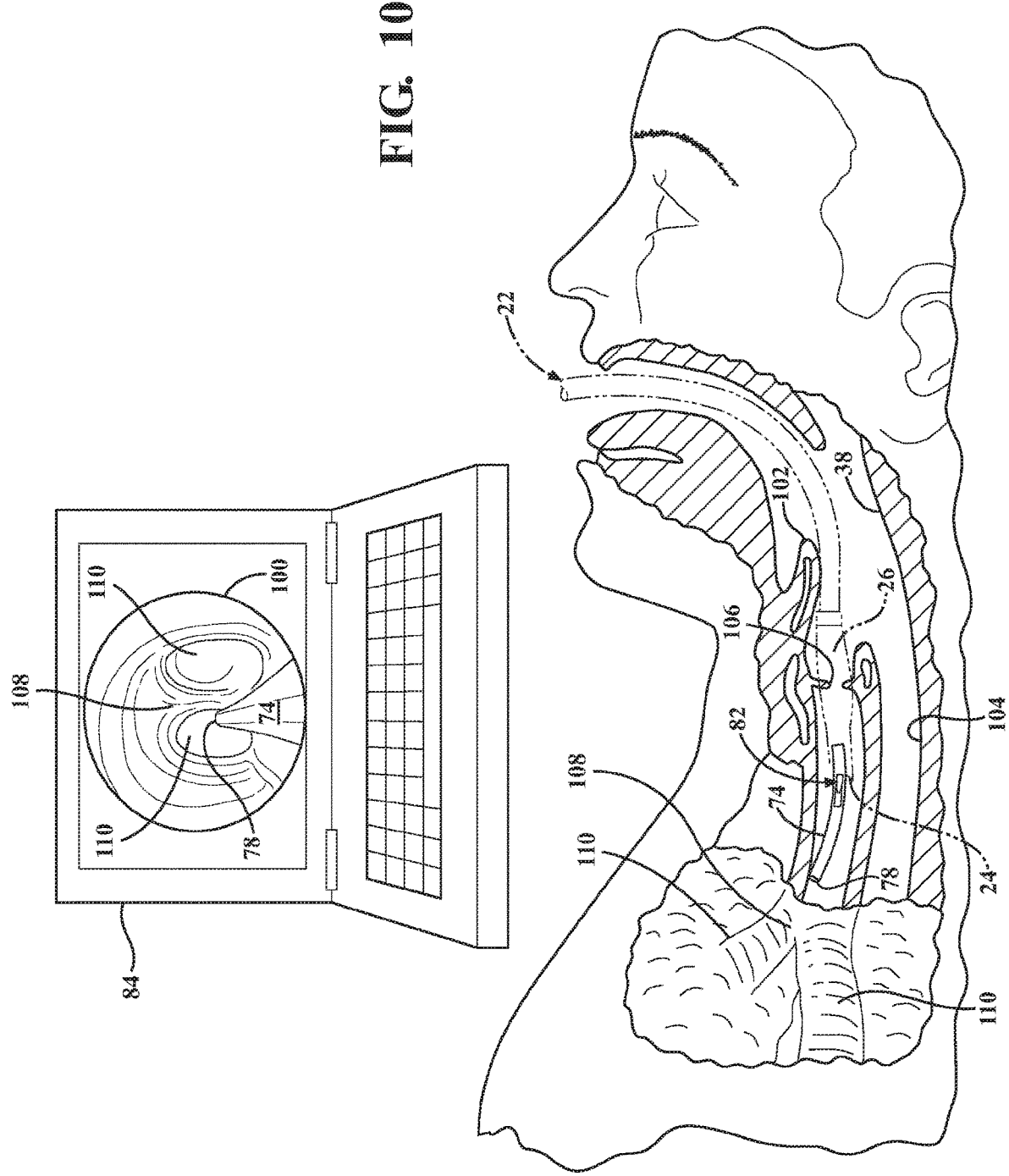
FIG. 10 is a view as in FIG. 8 where the leading end of the ET tube and stylet assembly are approaching the carina, and an exemplary view from the video camera projected onto a nearby monitor or screen.

Moreover, the strategic location of the lens pocket 80 will produce a uniquely foreshortened perspective of the distal tip 78, as can be seen in FIGS. 8-10. The foreshortened perspective of the distal tip 78 appearing on the remote monitor 84 has been found yield surprisingly intuitive benefits for under-trained users. For underlying reasons not yet fully understood, practitioners who do not perform enough intubation procedures to attain (or maintain) skill proficiency are better able to intuitively navigate through the trachea 38 based on visual cues observed through the remote monitor 84 because of the image of the end-piece 74 and even more particularly because of its foreshortened perspective. Possibly, the foreshortened perspective is effective because the nearest visible portion of the end-piece 74 moves very little if at all relative to the image capture device 82 by action of the remote actuator 50. However, movement of the distal tip 78 relative to the image capture device 82 will appear highly accentuated in the monitor 84 view due to the foreshortened perspective. Therefore, it may be the case that the live video feed image appearing in the monitor 84 will tend to under-state motion proximate the transition 76 (where the image capture device 82 is located) and over-state motion of the distal tip 78. It could be that this under-stating/over-stating of motion in the image appearing on the monitor 84 has the ability to instinctively compress the learning curve so that relatively under-trained people performing an intubation can avoid actions leading to failure.

As alluded to above, there is some advantage to locating the lens pocket 80 entirely within the end-piece 74 directly adjacent the transition 76. This advantage can be described with reference to FIGS. 4 and 6. Remembering that the main stem 68 of the steering shaft 36 is relatively rigid whereas the end-piece 74 is highly flexible, it will be appreciated that manipulation of the remote actuator 50 produces substantial displacement of the distal tip 78 but little to no displacement whatsoever in the main stem 68. In cases where the lens pocket 80 is located entirely within the end-piece 74, the lens pocket 80 will also experience some displacement when the remote actuator 50 is moved. The image capture device 82 is partially housed within, and mounted relative to, the lens pocket 80. When the lens pocket 80 moves, the image capture device 82 moves with so that the resulting image appearing on the remote monitor 84 will not register relative movement. It would be as if watching an image generated by a forward-looking camera located inside the cockpit of an airplane; the cockpit corresponding to the lens pocket 80. In that analogy, the image produced will not show any relative motion vis-à-vis the cockpit interior even through the airplane may be performing highly aerobatic maneuvers. In a similar way, the image capture device 82 will move with the lens pocket 80 when the lens pocket 80 is located entirely within the end-piece 74. The articulating distal tip 78 will be seen to move, but this movement is accentuated by the previously-described foreshortening perspective technique so that the screen image seen by the operator is favorably distorted in a way to enhances the intuitive learning curve. Another way to describe this phenomenon is that when the lens pocket 80 is located entirely within the end-piece 74, albeit adjacent the transition 76, the field of view FOV will move with operation of the remote actuator 50. However, because the lens pocket 80 is close to the transition 76, the amount of movement of the field of view FOV will always be less than the amount of movement of the distal tip 78. Therefore, the distal tip 78 will appear to move within the field of view FOV. And the appearance of movement of the distal tip 78 within the field of view FOV is somewhat over-emphasized by the foreshortening perspective technique described above.

As mentioned already, the image capture device 82 can take many different forms. Nevertheless, one example of an image capture device 82 is shown in longitudinal cross-section in FIG. 7. In this example, the image capture device 82 is a digital video camera having a generally cylindrical housing. The field of view FOV for this image capture device 82 is intentionally upwardly angled, however other applications may dictate differently angled or non-angled FOV's. Inside the housing, a stacked set of optical prism lenses 86 are positioned at its outward-looking end (left-hand side in FIG. 7). The prism lenses 86 are separated from a doublet lens 88 by a first lens spacer 90. The doublet lens 88 is separated from an infrared (IR) filter 92 by a second spacer 94. The rear end of the tubular housing forms a mounting space for image sensors 96, from which emanate a flexible circuit board 98. Typically, one or more signal wires will extend from the flexible circuit board 98 to transmit a video signal, commands and power.

In FIG. 8, an image 100 is depicted on the remote monitor 84 as produced by the image capture device 82 in the accompanying anatomical drawing. The image 100 corresponds to the instantaneous field of view of the image capture device 82. Inside the patient's trachea 38, the end-piece 74 of the stylet assembly 20 is approaching a first major obstacle—the epiglottis 102. The ET tube 22 must be expertly routed below the epiglottis 102 to avoid the possibility of soft-tissue damage. Because of the strategic location of the lens pocket 80, a foreshortened perspective of the end-piece 74 appears in the image 100 together with the epiglottis 102. The person performing the intubation procedure manipulates the remote actuator 50 to steer the distal tip 78 below the epiglottis 102.

FIG. 9 shows a further progression in the intubation procedure from FIG. 8. Here, the end-piece 74 of the stylet assembly 20 is shown approaching the next two major obstacles in the patient's trachea 38—the bifurcation leading to the esophagus 104 and shortly thereafter the vocal cords 106. To achieve a successful intubation placement, the ET tube 22 must be routed away from esophagus 104 and remain within the trachea 38. To avoid harm to the patient, the ET tube 22 must be routed with extreme care through the vocal cords 106. Because of the strategic location of the lens pocket 80, a foreshortened perspective of the end-piece 74 remains in the image 100 while also showing the bifurcation to the esophagus 104 and the vocal cords 106. The person performing the intubation procedure is able to intuitively steer the distal tip 78 along the desired path.

FIG. 10 shows a still further progression in the intubation procedure from FIG. 9, where the end-piece 74 is shown approaching its final destination at the carina 108. A primary concern at this late stage of the intubation procedure is when to stop. Ideally, the leading end of the ET tube 22 is placed just prior to the carina 108 so that both main bronchus passages 110 are accessible to the air eventually aspirated through the ET tube 22. If the ET tube 22 is pushed too deeply, one of the main bronchus passages 110 could be starved of air and/or injury could result to the patient. Because of the strategic location of the lens pocket 80, a foreshortened perspective of the end-piece 74 remains in the image 100 while also showing the carina 108. The person performing the intubation procedure uses the real-time visual image 100 to intuitively steer and stop the distal tip 78 and thereby achieve a successful placement of the ET tube 22. The cuff 26 is inflated thus holding the leading end 24 of the ET tube 22 in position (FIG. 2).

At this point in the intubation procedure, the stylet assembly 20 must be removed, leaving in place the ET tube 22. As diagrammed in FIG. 2, a quick and minimally disruptive decoupling of the stylet assembly 20 from the ET tube 22 is accomplished by a partial twist of the handle 34 followed by a pulling motion. The initial twisting motion breaks the friction between the collar connector 32 on the ET tube 22 and a collar seat 112 in the handle 34. The collar seat 112 is best shown in FIGS. 12 and 13 comprising a semi-circular opening sized and adapted for a light frictional (interference) fit with the cylindrical outer surface of a standard collar connector 32. Advantageously, the collar seat 112 holds the ET tube 22 in the handle 34 with sufficient grip to enable all of the normal stresses encountered during intubation procedures. At the collar connector 32/collar seat 112 interface, most of the axial forces will be compressive. A partition 114 is located in the handle 34 near the collar seat 112 to provide a back-stop for the collar connector 32. The steering shaft 36 passes centrally through the collar seat 112 in the handle 34, as well as through the partition 114. The frictional wedge of the collar connector 32 in the collar seat 112 thus provides a simple and convenient one-handed method to remove the stylet assembly 20.

In summation, the present invention is a medical device and/or method that is designed to improve the efficacy and safety of intubations, especially in the hands of less-skilled practitioners, and to reduce the training necessary to be successful.

The foregoing invention has been described in accordance with the relevant legal standards, thus the description is exemplary rather than limiting in nature. Variations and modifications to the disclosed embodiment may become apparent to those skilled in the art and fall within the scope of the invention. Furthermore, particular features of one embodiment can replace corresponding features in another embodiment or can supplement other embodiments unless otherwise indicated by the drawings or this specification.

What is claimed is:

1. A manually articulated stylet assembly for facilitating placement of an intubation device in a patient, said assembly comprising:
   at least one flexible motion transmitting element having a controlled end and a controlling end,
   a handle, a remote actuator supported on said handle for movement toward and away from at least one actuated position, said remote actuator including an anchor point connecting said controlling end of said at least one motion transmitting element,
   a steering shaft extending from said handle, said steering shaft having an elongated main stem defining a centerline along the length thereof, a flexible end-piece adjoining said main stem at a transition and extending along said centerline longitudinally therefrom to a distal tip, said controlled end of said at least one flexible motion transmitting element connected to said distal tip of said end-piece such that movement of said remote actuator causes a corresponding movement of said distal tip,
   an image capture device having a field of view, and
   a recessed lens pocket disposed in said steering shaft adjacent said transition and spaced from said distal tip, said lens pocket being laterally offset from said centerline for partially housing said image capture device in a forward-pointing direction with said field of view oriented to capture moving images of said distal tip in response to actuation of said remote actuator, said image capture device being fixedly mounted relative to said recessed lens pocket so as to produce, in use, an articulating foreshortened perspective of said flexible end-piece in which a nearest visible portion of said end-piece is generally stationary relative to said image capture device and said distal end of said end-piece will appear to move relative to said image capture device.

2. The assembly of claim 1, wherein said lens pocket is disposed in said end-piece, and said end-piece is continuously flexible between said transition and said distal tip.

3. The assembly of claim 1, wherein said end-piece has a pre-set curvature.

4. The assembly of claim 1, wherein said at least one flexible motion transmitting element comprises an upper flexible motion transmitting element and a lower flexible motion transmitting element, each of said upper and lower flexible motion transmitting elements comprising a respective controlled end and a controlling end.

5. The assembly of claim 4, wherein said handle has a hollow interior cavity, said remote actuator at least partially disposed in said interior cavity, said interior cavity including a journal for supporting said remote actuator for oscillating pivotal movement about a pivot axis, said remote actuator including upper and lower tracks for respectively supporting variable lengths of said upper and lower motion transmitting elements as said remote actuator is rotated about said pivot axis.

6. The assembly of claim 5, wherein said remote actuator includes a biasing member.

7. The assembly of claim 5, wherein said main stem includes longitudinally-extending upper and lower lumens establishing respective sliding guide paths for said upper and lower flexible motion transmitting elements, said upper and lower lumens are diametrically opposed from one another within an articulation plane, said articulation plane perpendicularly bisecting said pivot axis of said remote actuator.

8. The assembly of claim 5, wherein said anchor point generally coincides with said pivot axis.

9. The assembly of claim 4, wherein said main stem is tubular having a generally constant circular outside diameter along the longitudinal length thereof, said upper and lower lumens diametrically opposed from one another within an articulation plane, said end-piece having a generally constant circular outside diameter, said end-piece having upper and lower lumen extensions aligning with the respective said upper and lower lumens of said main stem to establish continuous sliding guide paths for said upper and lower flexible motion transmitting elements within said articulation plane, portions of said upper and lower flexible motion transmitting elements extending through said end-piece being maintained within said articulation plane.

10. The assembly of claim 1, wherein said remote actuator includes at least one track for supporting variable lengths of said at least one motion transmitting element as said remote actuator is moved, said at least one track is semi-circular and concentrically located about a pivot axis, said at least track including a driving edge.

11. The assembly of claim 1, wherein said at least one flexible motion transmitting element comprises an upper flexible motion transmitting element and a lower flexible motion transmitting element, said lens pocket is disposed in said end-piece generally equally spaced between said upper and lower flexible motion transmitting elements, said main stem having longitudinally-extending upper and lower lumens establishing respective sliding guide paths for said upper and lower flexible motion transmitting elements, said upper and lower lumens are diametrically opposed from one another within an articulation plane.

12. The assembly of claim 11, wherein said main stem is tubular having a generally constant circular outside diameter along the longitudinal length thereof, said end-piece having a generally constant circular outside diameter, said end-piece having upper and lower lumen extensions aligning with the respective said upper and lower lumens of said main stem to establish continuous sliding guide paths for said upper and lower flexible motion transmitting elements within said articulation plane, portions of said upper and lower flexible motion transmitting elements extending through said end-piece being maintained within said articulation plane.

13. The assembly of claim 11, wherein said handle has a hollow interior cavity.

14. The assembly of claim 13, wherein said remote actuator includes a thumb tab exposed outside of said interior cavity of said handle.

15. The assembly of claim 1, wherein said main stem has at least one longitudinally-extending lumen establishing a sliding guide path for said at least one motion transmitting element.

16. The assembly of claim 14, wherein said main stem has at least one longitudinally-extending lumen establishing a sliding guide path for said at least one motion transmitting element, said at least one lumen is disposed within an articulation plane, said articulation plane perpendicularly bisecting said thumb tab.

17. A manually articulated stylet assembly for facilitating placement of an intubation device in a patient, said assembly comprising:

an upper flexible motion transmitting element and a lower flexible motion transmitting element, each of said upper and lower flexible motion transmitting elements comprising a respective controlled end and a respective controlling end, a handle having a hollow interior cavity, a plurality of guides disposed in said interior cavity for establishing guide paths for said upper and lower flexible motion transmitting elements, a remote actuator supported on said handle for movement toward and away from at least one actuated position, said interior cavity including a journal for supporting said remote actuator for pivotal movement about a pivot axis, said remote actuator having a generally circular interface disposed in rotational sliding contact with said journal, said remote actuator including a thumb tab exposed outside of said interior cavity of said handle, said remote actuator including upper and lower tracks for respectively supporting variable lengths of said upper and lower motion transmitting elements as said remote actuator is rotated about said pivot axis, said upper and lower tracks being semi-circular and concentrically located about said pivot axis, said remote actuator including an anchor point for connecting said controlling ends of said upper and lower motion transmitting elements, said anchor point generally coinciding with said pivot axis, said remote actuator including a biasing member disposed between said anchor point and said tracks, said biasing member having a generally elliptical configuration, a steering shaft extending from said handle, said steering shaft having an elongated tubular main stem defining a centerline along the length thereof, said main stem having longitudinally-extending upper and lower lumens establishing respective sliding guide paths for said upper and lower flexible motion transmitting elements, said upper and lower lumens being diametrically opposed from one another within an articulation plane, said centerline contained within said articulation plane, said articulation plane perpendicularly bisecting said pivot axis of said remote actuator, said main stem having a generally constant circular outside diameter along the longitudinal length thereof, a flexible end-piece adjoining said main stem at a transition and extending along said centerline longitudinally therefrom to a distal tip, said end-piece having a generally constant circular outside diameter substantially equal to the outside diameter of said main stem, said end-piece having a pre-set curvature laying within said articulation plane, portions of said upper and lower flexible motion transmitting elements extending through said end-piece being maintained within said articulation plane, said end-piece having upper and lower lumen extensions aligning with the respective said upper and lower lumens of said main stem to establish continuous sliding guide paths for said upper and lower flexible motion transmitting elements within said articulation plane, said controlled ends of said upper and lower flexible motion transmitting elements directly fixedly connected to said distal tip of said end-piece, a lens pocket disposed in said end-piece adjacent said transition and spaced from said distal tip, said lens pocket being laterally offset from said articulation plane, said lens pocket being generally equally spaced between said upper and lower flexible motion transmitting elements, and an image capture device disposed in said lens pocket, said image capture device having a field of view directed toward said distal tip, at least one signal wire extending from said image capture device to transmit a video signal to a remote viewing monitor.

\* \* \* \* \*